United States Patent
Schomacker et al.

(10) Patent No.: US 9,987,088 B2
(45) Date of Patent: ***Jun. 5, 2018

(54) REDUCTION OF PAIN THROUGH LOWER FLUENCE RATES AND LONGER TREATMENT

(71) Applicant: CANDELA CORPORATION, Wayland, MA (US)

(72) Inventors: Kevin Schomacker, Maynard, MA (US); James C. Hsia, Weston, MA (US)

(73) Assignee: Candela Corporation, Wayland, MA (US)

( * ) Notice: Subject to any disclaimer, the term of this patent is extended or adjusted under 35 U.S.C. 154(b) by 163 days.

This patent is subject to a terminal disclaimer.

(21) Appl. No.: 14/943,265

(22) Filed: Nov. 17, 2015

(65) Prior Publication Data
US 2016/0089202 A1    Mar. 31, 2016

Related U.S. Application Data

(62) Division of application No. 13/110,850, filed on May 18, 2011, now Pat. No. 9,308,046.

(60) Provisional application No. 61/345,834, filed on May 18, 2010.

(51) Int. Cl.
*A61B 18/18*     (2006.01)
*A61B 18/20*     (2006.01)
*A61B 18/00*     (2006.01)

(52) U.S. Cl.
CPC .. *A61B 18/203* (2013.01); *A61B 2018/00023* (2013.01); *A61B 2018/00029* (2013.01); *A61B 2018/00464* (2013.01); *A61B 2018/1807* (2013.01)

(58) Field of Classification Search
CPC ........ A61B 18/203; A61B 2018/00023; A61B 2018/00029; A61B 2018/00464; A61B 2018/1807
USPC ............................................................ 607/89
See application file for complete search history.

(56) References Cited

U.S. PATENT DOCUMENTS

| | | | |
|---|---|---|---|
| 9,308,046 B2* | 4/2016 | Schomacker ........ | A61B 18/203 |
| 2004/0093042 A1* | 5/2004 | Altshuler ............. | A61B 18/203 |
| | | | 607/88 |
| 2006/0016790 A1* | 1/2006 | Yeik ...................... | A61B 18/20 |
| | | | 219/121.61 |

FOREIGN PATENT DOCUMENTS

WO    2010031777 A2    3/2010

* cited by examiner

*Primary Examiner* — Aaron Roane
(74) *Attorney, Agent, or Firm* — Manelli Selter PLLC; Edward J. Stemberger

(57) ABSTRACT

A method of treating a subcutaneous fat region is provided. The method includes generating electromagnetic radiation having a wavelength of about 1,200 nm to about 1,230 nm and delivering an average power density of less than or equal to about 2.3 W/cm² of the electromagnetic radiation to the subcutaneous fat region for at least 300 seconds. The method also includes cooling an epidermal region and at least a portion of a dermal region overlying the subcutaneous fat region for at least a portion of the at least 300 seconds. The method further includes causing necrosis of at least one fat cell in the subcutaneous fat region.

16 Claims, 13 Drawing Sheets

2.0 mm Dermis 3.0 mm Dermis

REDUCTION OF PAIN THROUGH LOWER FLUENCE RATES AND LONGER TREATMENT

CROSS REFERENCE TO RELATED APPLICATIONS

This application claims the benefit of and priority to U.S. Provisional Application No. 61/345,834 filed May 18, 2010, which is owned by the assignee of the instant application and the disclosure of which is incorporated herein by reference in its entirety.

FIELD OF THE INVENTION

The invention relates generally to a process and system for delivering laser radiation to skin as a means for selectively heating subcutaneous fatty tissue, and more particularly, to causing thermal injury to subcutaneous fatty tissue without the need for anesthetics and without causing intolerable pain to the subject.

BACKGROUND OF THE INVENTION

Prior work has shown selective laser damage to subcutaneous fat without causing severe dermal damage or scarring. Using a 1210 nm near-infrared (NIR) diode laser, prior study has found an optimum fat selective dose of 80 J/cm$^2$ based on a 10 mm spot size, 3 s exposure and contact cooling. Even though the laser treatments are safe, they are also painful. In continuing to optimize 1210 nm NIR laser for the treatment of cellulite and fat reduction, the treatment beam diameter was increased to 40 mm and the pulse duration was increased to 40 s. Tissue viability studies of freshly excised porcine and human skin using these treatment parameters found laser doses between 140-180 J/cm$^2$ were needed to obtained sufficient thermal damage to subcutaneous fat while avoiding damage to the epidermis and dermis. These parameters can be too painful and not easily tolerated by subjects.

Other treatments of subcutaneous fat are ineffective and can cause adverse effects. For example, U.S. Pat. No. 7,351,252 to Altshuler et al. ("Altshuler") describes treating a desired region of tissue by applying optical radiation to reach the depth of the region. Treatment regions disclosed by Altshuler include the reticular dermis region, the dermis-subcutaneous fat junction, and the subcutaneous fat region. For each of the three regions, Altshuler discloses a set of treatment parameters, including radiation exposure time and power density, that are used when pre-cooling is applied to the surface of the skin and a different set of parameters when treatment is performed without surface pre-cooling. FIG. 1 shows a diagram of treatment parameters disclosed by Altshuler when pre-cooling is not applied, the skin surface is cooled to 5° C. during radiation treatment and the laser wavelength is about 1.15-1.23 nm. The area 102 represents the range of radiation exposure time (2-65 s) versus the range of power density (2.5-50 W/cm$^2$) disclosed by Altshuler for treating the reticular dermis region (1-3 mm depth) and the dermis-subcutaneous fat junction (2-5 mm depth). The area 106 represents the range of radiation exposure time (65-270 s) versus the range of power density (0.5-20 W/cm$^2$) disclosed by Altshuler for treating the subcutaneous fat region (5-10 mm depth).

Studies have shown that more than 75% of the areas 102 and 106 taught by Altshuler are ineffective and/or can cause adverse skin effects. In FIG. 1, the solid curve 110 represents the lower bound of the therapeutic range for which treatment is effective. The solid curve 114 represents the upper bound of the therapeutic range for which treatment is effective. The solid curves 110 and 114 were calculated based on a thermal model of the skin and clinical results.

As shown by FIG. 1, a large portion of each of the areas 102 and 106 is outside of the effective treatment zone bound by the curves 110 and 114. In particular, portion 102a of the area 102 below the curve 110 indicates ineffective parameters for treating the reticular dermis region and the dermis-subcutaneous fat junction according to Altshuler. Portion 102b of the area 102 above the curve 114 indicates harmful parameters for treating the reticular dermis region and the dermis-subcutaneous fat junction according to Altshuler. Similarly, in the area 106, portion 106a below the curve 110 indicates ineffective parameters for treating the subcutaneous fat region according to Altshuler. Portion 106b above the curve 114 indicates harmful parameters for treating subcutaneous fat region according to Altshuler. Therefore, based on the teachings of Altshuler, a practitioner cannot discern the effective therapeutic range for treating different regions of tissue and is likely to provide ineffective or adverse treatment as a result. Adverse effects can include minor epidermal blistering to more severe full-thickness skin burns and ulcerations.

SUMMARY OF THE INVENTION

The invention, in various embodiments, features treatments of subcutaneous fat in biological tissue. A treatment can cause pain-tolerant necrosis in subcutaneous fat region of the tissue, thereby reducing the number of fat cells in the tissue. In addition, the treatment methods are safer and more effective than prior art treatments. A treatment can be used to contour or re-contour body fat, which can include non-invasive shaping, fat removal, and skin-tightening.

In one aspect, a method of treating a subcutaneous fat region is provided. The method includes generating electromagnetic radiation having a fat-selective wavelength of about 1,200 nm to about 1,230 nm and delivering an average power density of less than or equal to 2.3 W/cm$^2$ of the electromagnetic radiation to the subcutaneous fat region for at least 300 seconds. The method also includes cooling an epidermal region and at least a portion of a dermal region overlying the subcutaneous fat region for at least a portion of the at least 300 seconds and causing necrosis of at least one fat cell in the subcutaneous fat region.

In another aspect, a method of treating a subcutaneous fat region is provided. The method includes generating electromagnetic radiation having a non-fat selective wavelength and delivering the electromagnetic radiation to the subcutaneous fat region for at least 300 seconds. The method also includes cooling an epidermal region and at least a portion of a dermal region overlying the subcutaneous fat region for at least a portion of the at least 300 seconds and causing necrosis of at least one fat cell in the subcutaneous fat region. The method can further include deliver an average power density of less than or equal to 4.0 W/cm$^2$ of the non-fat-selective electromagnetic radiation.

In some embodiments, the electromagnetic radiation is delivered in three consecutive time intervals. During a first time interval, the subcutaneous fat region is exposed to the electromagnetic radiation at a first power density. During a second time interval, the subcutaneous fat region is exposed to the electromagnetic radiation while the electromagnetic radiation decreases from the first power density to a second power density. During a third time interval, the subcutaneous fat region is exposed to the electromagnetic radiation at the second power density. The first time interval is shorter than the sum of the second time interval and the third time interval.

In another aspect, a method of applying electromagnetic radiation to a subcutaneous fat region is provided. The method includes exposing the subcutaneous fat region to the electromagnetic radiation having a first power density for a first time interval. During a second time interval, the first power density of the electromagnetic radiation is lowered to a second power density while exposing the subcutaneous fat region to the electromagnetic radiation. For a third time interval, the subcutaneous fat region is exposed to the second power density. The first time interval is shorter than the sum of the second and third time intervals.

In another aspect, an apparatus for applying electromagnetic radiation to a subcutaneous fat region is provided. The apparatus includes a source of electromagnetic radiation and a delivery device coupled to the source. The apparatus also includes a controller configured to adjust the source so that the subcutaneous fat region is exposed to the electromagnetic radiation having a first power density for a first time interval, the first power density of the electromagnetic radiation is lowered, during a second time interval, to a second power density while the subcutaneous fat region is exposed to the electromagnetic radiation, and the subcutaneous fat region is exposed at the second power density for a third time interval. The first time interval is shorter than the sum of the second and third time intervals.

In yet another aspect, a computer program product, tangibly embodied in a non-transitory computer-readable storage medium, is provided. The computer program product contains instructions operable to cause a data processing apparatus to control an optical device to deliver electromagnetic radiation having a first power density for a first time interval to expose a subcutaneous fat region to the electromagnetic radiation. The optical device can be controlled to lower, during a second time interval, the first power density of the electromagnetic radiation to a second power density while the subcutaneous fat region is exposed to the electromagnetic radiation. In addition, the optical device can be controlled to deliver the electromagnetic radiation to the subcutaneous fat region at the second power density for a third time interval. The first time interval is shorter than the sum of the second and third time intervals. In some embodiments, the computer program product can receive information from one or more built-in sensors or from an operator about the thickness of a subject's overlying skin. The computer program product can use the information to adjust the power density applied to the subject accordingly.

In other examples, any of the aspects above can include one or more of the following features. The fat-selective wavelength of the electromagnetic radiation can be about 875 nm to about 950 nm or about 1175 nm to about 1250 nm. In some embodiments, the fat-selective wavelength of the electromagnetic radiation is about 900 nm to about 940 nm or about 1200 nm to about 1240 nm. In some embodiments, the non-fat-selective wavelength is about 950 nm to about 1090 nm or about 1100 nm to about 1160 nm. The non-fat-selective wavelength can be about 950 nm to about 1180 nm.

In some embodiments, the electromagnetic radiation is delivered to the subcutaneous fat region for about 300 seconds to about 400 seconds. In some embodiments, the electromagnetic radiation is delivered to the subcutaneous fat region greater than or equal to 3 mm below a surface of skin. At least one fat cell can be damaged so that lipid contained within can escape and at least a portion of the lipid can be carried away from the subcutaneous fat region.

In some embodiments, the electromagnetic radiation is delivered to the subcutaneous fat region for about 20 minutes to about 30 minutes. The electromagnetic radiation can be delivered to the targeted treatment region via a body-fitting garment worn by the subject. The garment can include a means for delivering the electromagnetic radiation and/or built-in laser diodes, light emitting diodes, or fiber-optics configured to deliver light from a source. The source can be separate from the garment or constructed into the garment. The garment can include a cooling system for cooling the epidermis and parts of the dermis. The garment may be supplied as part of an exercising apparatus, in which case the time of electromagnetic heating can correspond to a user-selected exercising regiment.

In some embodiments, the electromagnetic radiation includes multiple pulses of electromagnetic radiation. If pulses of the electromagnetic radiation are about 1210 nm, the average power density can be about 0.5 W/cm$^2$ to about 2.5 W/cm$^2$. The peak power density can exceed 2.5 W/cm$^2$.

In some embodiments, the electromagnetic radiation includes multiple pulses of 925 nm electromagnetic radiation. The average power density can be about 0.5 W/cm$^2$ to about 3.5 W/cm$^2$. The peak power density can exceed 3.5 W/cm$^2$.

In some embodiments, the electromagnetic radiation includes multiple pulses of 1140 nm electromagnetic radiation. The average power density can be about 0.5 W/cm$^2$ to about 3.5 W/cm$^2$. The peak power density can exceed 3.5 W/cm$^2$.

In some embodiments, the electromagnetic radiation includes multiple pulses of 1064 nm electromagnetic radiation. The average power density can be about 0.5 W/cm$^2$ to about 4.0 W/cm$^2$. The peak power density can exceed 4.0 W/cm$^2$.

In some embodiments, the electromagnetic radiation includes multiple pulses of 975 nm electromagnetic radiation. The average power density can be about 0.5 W/cm$^2$ to about 3.5 W/cm$^2$. The peak power density exceeds 3.5 W/cm$^2$.

In some embodiments, the average power density is adjusted based on a thickness of skin overlying the subcutaneous fat region.

In some embodiments, the electromagnetic radiation is delivered simultaneously to a surface of skin overlying the subcutaneous fat region and the surface of skin having an area of at least about 10 cm$^2$.

In various embodiments, the electromagnetic radiation is delivered in the absence of precooling of the epidermal region and the portion of the dermal region overlying the subcutaneous fat region. In various embodiments, the epidermal region and at least a portion of the dermal region overlying the subcutaneous fat region is cooled during electromagnetic radiation delivery. The electromagnetic radiation can be delivered in the absence of an anesthetic.

In some embodiments, a skin region overlying the subcutaneous fat region is massaged prior to, during or after delivery of the electromagnetic radiation.

In some embodiments, the sum of the first, second and third time intervals can be greater than 300 seconds. The sum of the first, second and third time intervals can be less than 300 seconds. The sum of the first, second and third time intervals can be about 165 seconds to about 300 seconds.

In some embodiments, the first power density is about 4 W/cm$^2$, the first time interval is about 13 seconds, the second power density is about 2 W/cm$^2$ and the sum of the second and third time intervals is about 92 seconds. In some embodiments, the first power density is about 4 W/cm², the first time interval is about 13 seconds, the second power density is about 2 W/cm² and the sum of the second and third time intervals is about 240 seconds.

In some embodiments, the first power density of the electromagnetic radiation is lowered to the second power density in a continuous manner. In some embodiments, the first power density of the electromagnetic radiation is lowered to the second power density in one or more discrete intensity levels.

In some embodiments, a temperature of at least a portion of a dermal region overlying the subcutaneous fat region is below about 44° C. during at least one of the first, second or third time interval.

In some embodiments, the first time interval is shorter than the second time interval. In some embodiments, the subcutaneous fat region is exposed to the electromagnetic radiation at a third power density during a fourth time interval, and the third power density is higher than the second power density but lower than the first power density. The third power density of the electromagnetic radiation can be increased in a continuous manner. The third power density of the electromagnetic radiation can be increased in one or more discrete intensity levels. The third power density can be raised in a manner that is pain-tolerable to the subject.

Other aspects and advantages of the invention will become apparent from the following detailed description, taken in conjunction with the accompanying drawings, illustrating the principles of the invention by way of example only.

BRIEF DESCRIPTION OF THE DRAWINGS

The advantages of the invention described above, together with further advantages, may be better understood by referring to the following description taken in conjunction with the accompanying drawings. The drawings are not necessarily to scale, emphasis instead generally being placed upon illustrating the principles of the invention.

FIGS. 4A-1, 4A-2, 4A-3 and 4B show experimental and computational results for treating fatty tissue.

DETAILED DESCRIPTION OF THE INVENTION

To reduce to the number of fat cells in biological tissue, radiation can be used to treat the tissue by selectively heating the subcutaneous fat region to induce fat necrosis without damaging the dermis and epidermis. Such treatment damages the fat cells so that lipid contained within can escape and at least a portion of the lipid can be carried away from a treatment region.

Based on the Arrhenius integral for predicting thermal damage, the onset and amount of damage are dependent both on tissue temperature and the time spent at that temperature. In particular, fat necrosis can be caused at lower power densities if exposure times are longer. Irradiation at lower power densities is advantageous because lower power densities generate lower temperatures, particularly in the dermis, which are more pain tolerant to a subject. Therefore, during treatment, a lower power density of radiation can be used, thereby decreasing the temperature rise in tissue to a level that is tolerable to the subject. The power density can be maintained at that temperature for a time sufficient to cause the desired damage. Based on thermal models, viability studies with excised porcine skin, and preliminary dosing in humans, a range of fluence rates and treatment durations have been identified that can be tolerated yet effective at inducing selective necrosis to subcutaneous fat while sparing the dermis and epidermis from injury.

For example, laser treatment can involve keeping the temperature in the dermal region below about 44° C., which is below the threshold for type 2 A-fiber nociceptors (the first heat-pain threshold occurring about 47° C.), while maintaining the temperature in the subcutaneous fat region to about 50° C. or greater to cause damage to this region. The exposure time is then determined by the Arrhenius time-temperature principle and can be around 300 to 400 seconds for a treatment temperature of about 50° C.

Figure 1:
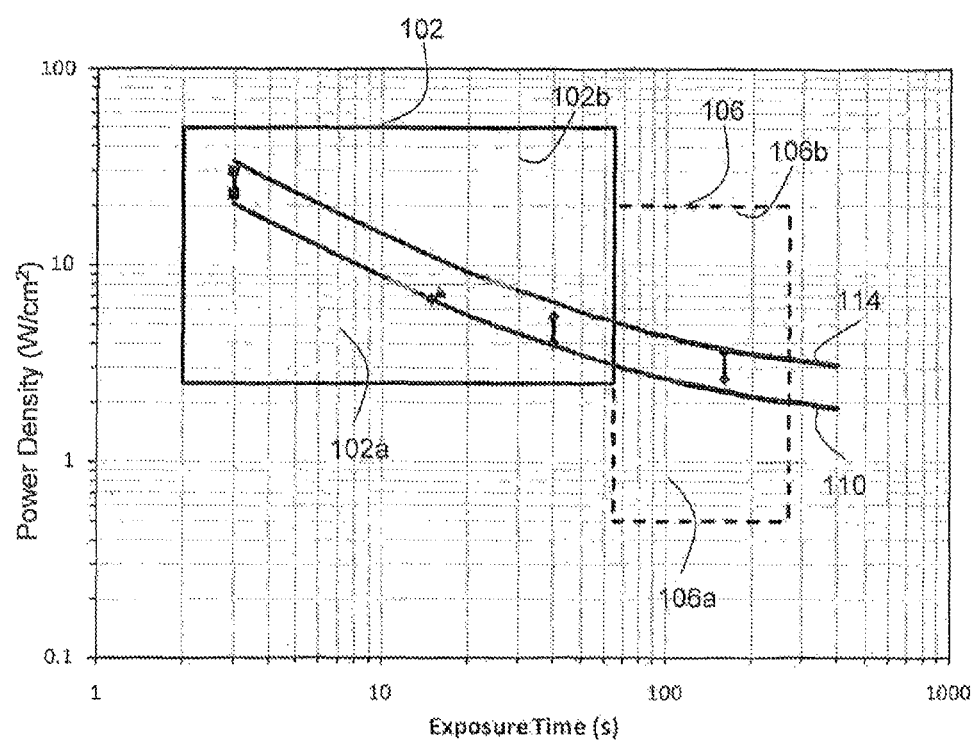
FIG. 1 shows a diagram of treatment parameters.

FIG. 1 shows an effective therapeutic range defined by curves 110 and 114 for treating 2 mm-thick skin using a 1210 nm wavelength and at various exposure durations and power densities. The therapeutic range of FIG. 1 is obtained in the absence of pre-cooling and with surface cooling of 5° C. applied during treatment. To treat subcutaneous fat in the 2 mm-thick skin without having to use anesthetics as a part of the procedure, power density of about 2 W/cm² or less can be selected, which is pain-tolerant to most subjects. Due to the low power density, exposure duration of about 300 s or greater can be used to satisfy the time-temperature behavior described by Arrhenius. The pain-tolerant power density can be dependent on skin thickness and the subject's tolerance to pain. Therefore the power density and the treatment time can be adjusted accordingly. In some embodiments, the curves 110 and 114 defining the effective therapeutic range change depending on whether cooling is applied before, during or after laser treatment and the temperature at which the skin is cooled.

A clinical study was performed where the abdominal skin of human subjects was treated using various durations of laser exposure at varying power densities. For example, the square, diamond and triangle symbols in FIG. 1 represent sample treatment data in human volunteers where fat necrosis was induced without causing adverse skin effects such as full-thickness burns leading to ulceration.

In some embodiments, to minimize the treatment time, higher initial laser powers can bring the temperature of tissue up quickly. To prevent exceeding a predetermined temperature (e.g., about 44° C. in the dermis), the power density of the electromagnetic radiation can be lowered and/or stepped down for a time period or the remainder of the treatment period. This approach generates similar thermal damage zones as the previous approach, but using a shorter treatment time. An additional increase in the treatment spot further decreases treatment times by reducing the number of treatment spots needed to cover the treatment area.

For example, the subcutaneous fat region of biological tissue is exposed to the electromagnetic radiation having a first intensity for a first time interval to quickly bring up the temperature of the subcutaneous fat region. The first intensity of the electromagnetic radiation is then lowered, during a second time interval, to a second intensity while exposing the subcutaneous fat region to the electromagnetic radiation. The subcutaneous fat region is exposed at the second intensity for a third time interval. The first time interval is shorter than a sum of the second and third time intervals, during which a higher initial laser power density is used.

The treatment period, including the first, second and third time intervals, can be at least 300 seconds. In some embodiments, the treatment period is less than 300 seconds, such as about 165 seconds to about 300 seconds. In general, the overall treatment time can be reduced due to the initial elevation of power density during the first time interval. In addition, this treatment is pain tolerant to a subject because the rise and fall of the initial power density is relatively short in comparison to the entire treatment period such that it is bearable to the subject. When providing treatment with a 4 cm diameter laser beam, for example, the first power level can be about 50 W, and the first time interval can be about 13 seconds, the second power level can be about 26 W, and the sum of the second and third time intervals can be about 92 seconds.

The first intensity of the electromagnetic radiation can be lowered to the second intensity in a continuous manner. The first intensity of the electromagnetic radiation can be lowered to the second intensity in one or more discrete intensity levels. The first time interval can be shorter than the second time interval. The first time interval can be shorter than the third time interval.

The temperature of the overlying skin tissue can be maintained below about 44° C. during at least one of the first, second or third time interval. The temperature of the overlying skin tissue can be maintained below about 44° C. during at least two of the first, second or third time interval. The temperature of the overlying skin tissue can be maintained below about 44° C. during all three of the first, second and third time intervals.

The biological tissue can be exposed to the electromagnetic radiation at a third power density during a fourth time interval. The third power density can be higher than the second power density, but lower than the first power density. Such rise in power density at the end of the third time interval is tolerable to a subject because the subject has already built up a certain paint threshold caused by overstimulated nociceptors at that point during treatment. Hence, no additional pain is experienced by the subject with the increase in power density. Such increase can further reduce the overall treatment time, which can be about 120 seconds to about 300 seconds. The third power density of the electromagnetic radiation can be increased in a continuous manner. The third power density of the electromagnetic radiation can be increased in one or more discrete intensity levels.

In some embodiments, a controller is used to automate the treatment process. The controller can automatically initiate the radiation exposure sequence after detecting that the skin has established full contact with cooling plate, or if vacuum is used to draw the skin into contact, when sufficient vacuum is applied to the skin of a subject. The controller can dynamically select the power density and exposure duration for delivering electromagnetic radiation to a subcutaneous fat region. If different power densities are used for different time intervals during treatment, the controller can also automatically determine the optimal power density and exposure time for each time interval.

In addition, the power density and exposure duration can be determined based on the thickness of the skin. The intensity of light reaching the subcutaneous layer decreases with increasing overlying skin thickness due to increase light scattering and absorption in skin, so increased power is required to cause sufficient thermal damage in the subcutaneous fat. Therefore, the thickness of the skin can be measured over the area of the body to be treated, such that the treatment fluence and exposure time can be selected and controlled for each individual and the body area to be treated. In some embodiments, skin thickness can be measured using ultrasonography at about 10 to 20 MHz for example.

The electromagnetic radiation can be delivered to the subcutaneous region in the absence of anesthetic. The electromagnetic radiation can be delivered to the subcutaneous region in the absence of pre-cooling of the epidermal region or the portion of the dermal region overlying the subcutaneous region. In some embodiments, surface cooling is applied to the epidermal region or the portion of the dermal region overlying the subcutaneous region for at least a portion of the time during which the subcutaneous fat region is treated with electromagnetic radiation. Surface cooling substantially prevents thermal damage to the superficial skin layers (epidermis and dermis). In some examples, the skin can be cooled to about 0 to about 10° C. (preferably, about 5° C.) during treatment. Contact cooling or cryogen spray cooling can be used. Contact cooling can provide for cooling to deeper depths.

Surface cooling is accomplished with a sapphire optical window generally cooled to about 5° C. and placed in contact with skin. Vacuum suction can be applied to the skin surface to ensure good contact with the cooled sapphire window. A second optical window can create a cooling chamber between the two windows from which a refrigerant such as cooled Fluorinert, cooled water, or another cryogenic fluid can flow. Atmospheric water vapor condenses on the outer surface of this cooling chamber, which can potentially absorb and scatter the laser treatment beam. Therefore, a third optical window can be used to form a second chamber filled with a thermally insulating gas such as argon, krypton, dry nitrogen or vacuum to minimize condensation on the exterior window. Details regarding surface cooling are provided below with reference to FIG. 9.

The following example shows that longer treatment duration at a lower power density causes a similar zone of thermal fat damage when compared to a shorter treatment duration at a higher power density. Yet, for tissues treated at the lower power density, the peak temperature in the dermis is much lower, thereby avoiding unbearable pain to a subject.

A finite element computer model was used to calculate temperature rises in tissues for 40 s and 120 s laser pulses and predict resulting tissue damages. The model was designed for a collimated 40 mm diameter laser beam incident onto the skin surface and includes a sapphire window cooled to 5° C. A two-layer tissue geometry was used to model thermal and optical properties of dermis and subcutaneous fat. The size of the tissue slab was 70 mm×70 mm×10 mm. The thickness of the dermal layer is variable and was typically set to 1.4 to 3 mm based on data collected from human volunteers as shown in Table 1.

TABLE 1

| | Skin thickness measured in normal volunteers Mean +/- STD (mm) | | | | | |
|---|---|---|---|---|---|---|
| Gender | Abdomen | Upper Arm | Posterior Thigh | Flank | Love Handle | Submental Neck |
| Male | 2.4 +/- 0.4 | 1.8 +/- 0.4 | 2.2 +/- 0.4 | 3.2 +/- 0.6 | 2.5 +/- 0.6 | 1.7 +/- 0.1 |
| Female | 1.9 +/- 0.5 | 1.2 +/- 0.2 | 1.6 +/- 0.2 | 2.3 +/- 0.6 | 1.8 +/- 0.4 | 1.5 +/- 0.4 |

Figure 2A:
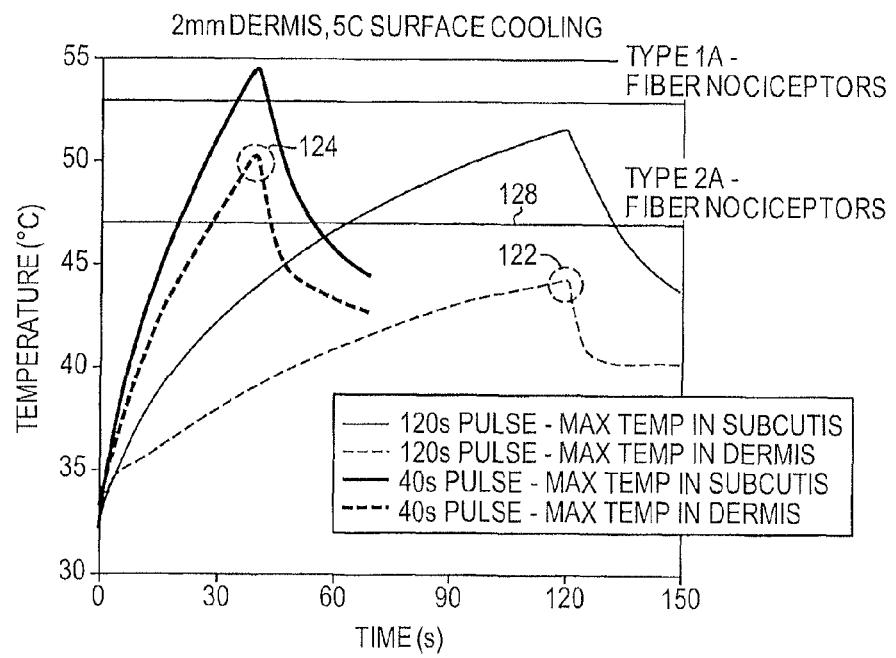
FIGS. 2A-2C show experimental and computational results for treating fatty tissue.
Figure 2B:
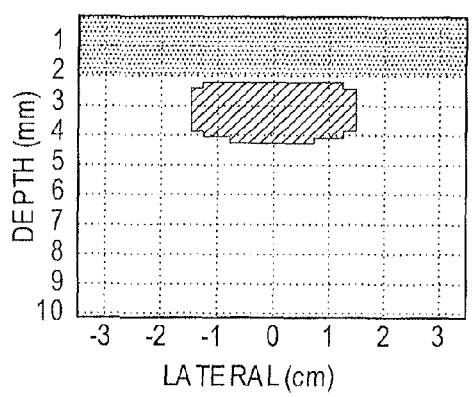
Figure 2C:
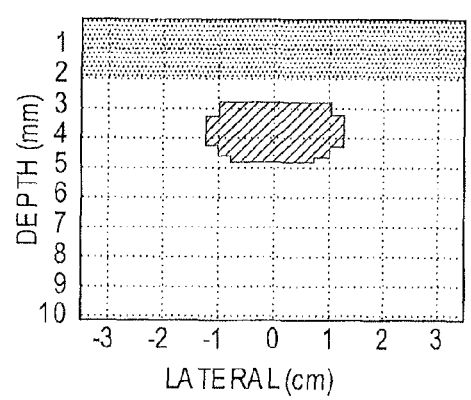

FIG. 2A shows the time evolution of peak temperatures in dermis and subcutis for 40 s and 120 s pulse durations. The applied laser power is 46 W (3.66 W/cm$^2$) and 29 W (2.31 W/cm$^2$) for the 40 s and 120 s pulses, respectively. The 46 W and 29 W laser power is adjusted such that the thickness of the predicted thermal damage zone is similar, as shown in FIGS. 2B and 2C. FIG. 2B shows the thermal damage predicted for the 40 s pulse duration and FIG. 2C shows the thermal damage predicted for the 120 s pulse duration. For both pulse durations, the peak temperature is sufficient to cause damage in the subcutaneous fat region while surface cooling is sufficient to protect the dermis from damage. However, as shown in FIG. 2A, the peak dermal temperature 122 where a majority of the heat pain receptors reside is drastically reduced for the 120 s pulse in comparison to the peak dermal temperature 124 for the 40 s pulse. In addition, the peak dermal temperature 122 of the 120 s pulse is well below the first pain threshold 128 at 47° C.

Therefore, it is predicted that even though approximately the same damage to the subcutaneous fat is caused by the two pulse durations, the longer 120 s pulse duration is expected to be much less painful. Another advantage of the longer 120 s pulse is that the zone of thermal damage is deeper in the subcutaneous fat region, thus forming a wider zone of undamaged adipose tissue bordering the dermis. One disadvantage of using the longer 120 s pulse is a narrowing of the laser damage zone due to more sideway thermal diffusion that occurs over longer times. This disadvantage can be reduced by using larger diameter treatment beams.

Pain tolerance was verified from a number of volunteers. In general, subjects can take at most 20 s of the 40 s pulse before pain became unbearable, while the entire 120 s pulse was easily taken by the subjects, although some deep but tolerable pain was noted.

Figure 3A:
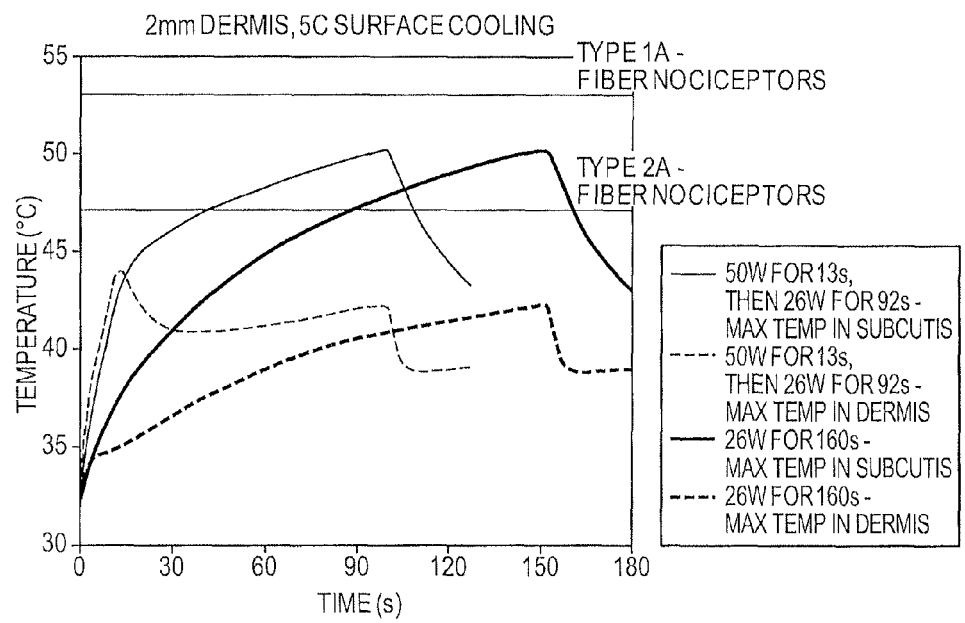
FIGS. 3A-3C show experimental and computational results for treating fatty tissue.
Figure 3B:
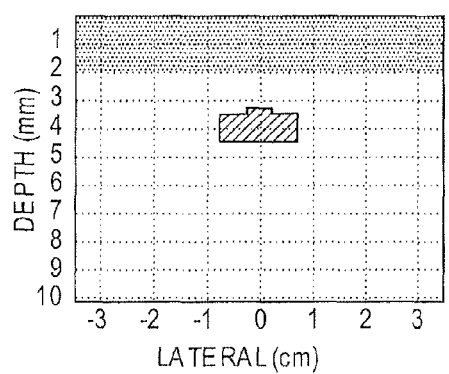
Figure 3C:
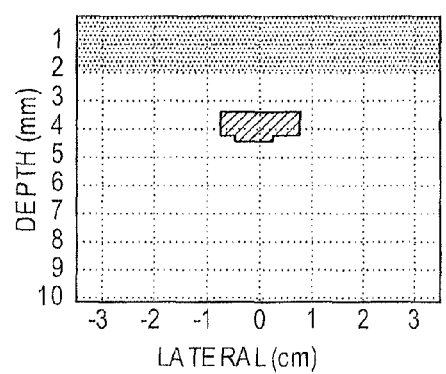

FIGS. 3A-C show the results of shortening the laser treatment time by using a higher initial laser power to quickly bring up tissue temperature, but preventing the temperature in the dermis from exceeding 44° C. The temperature is then lowered to a second laser power for the remainder of the treatment period. One disadvantage of the approach described above with reference to FIGS. 2A-C is that a longer treatment time is needed to cause sufficient thermal damage to tissue. To recover some of the lost time, an approach is used that includes starting treatment at a higher radiation power so as to raise temperature quickly, then lowering the power intensity to avoid high and painful peak temperatures in the dermis.

FIGS. 3A-C compare the results from two treatment schemes. Both treatments are designed to cause similar zones of thermal damage as predicted by a numerical model. The first treatment scheme treats tissue at a single power density, 2.1 W/cm$^2$ (26 W for a 40 mm spot) for 160 s. The second treatment scheme shortens the treatment time by 55 s by initially using a higher treatment power density, 4.0 W/cm$^2$ (50 W for a 40 mm spot) for 13 s. Then, to avoid exceeding 44° C. in the dermis, the treatment power density is lowered to 2.1 W/cm$^2$ for 92 s.

FIG. 3A shows the time evolution of maximum temperatures at the dermis and adipose tissue for the two treatment schemes. FIGS. 3B and 3C show the predicted damage zones for the first and second schemes, respectively. A comparison of FIGS. 3B and 3C reveals that the second scheme causes sufficient and similar subcutaneous fat damage as the first scheme. FIG. 3A shows that the second scheme only uses about 13 s to raise the temperature of the dermis and subcutaneous adipose tissue to 44° C., while the first scheme takes about 60 s. In addition, the total treatment time required using the second scheme is 105 s while the first scheme takes about 160 s.

The second treatment scheme can include multiple discrete stepped-down power levels or a continuous lowering of the laser power. In this example, the maximum dermal temperature drops rapidly once the power is lowered. A more gradual drop in power can also be tolerable to a subject and help to accelerate the rise in temperature in the subcutaneous fat region, thus further shortening the treatment time in comparison to using a more rapid drop. In some embodiments, the power is increased after a lowering period if pain is found to be tolerable. It has been shown that pain at the first nociceptor threshold dulls over time, thus allowing for an increase in power applied.

Figures 1, 4A:
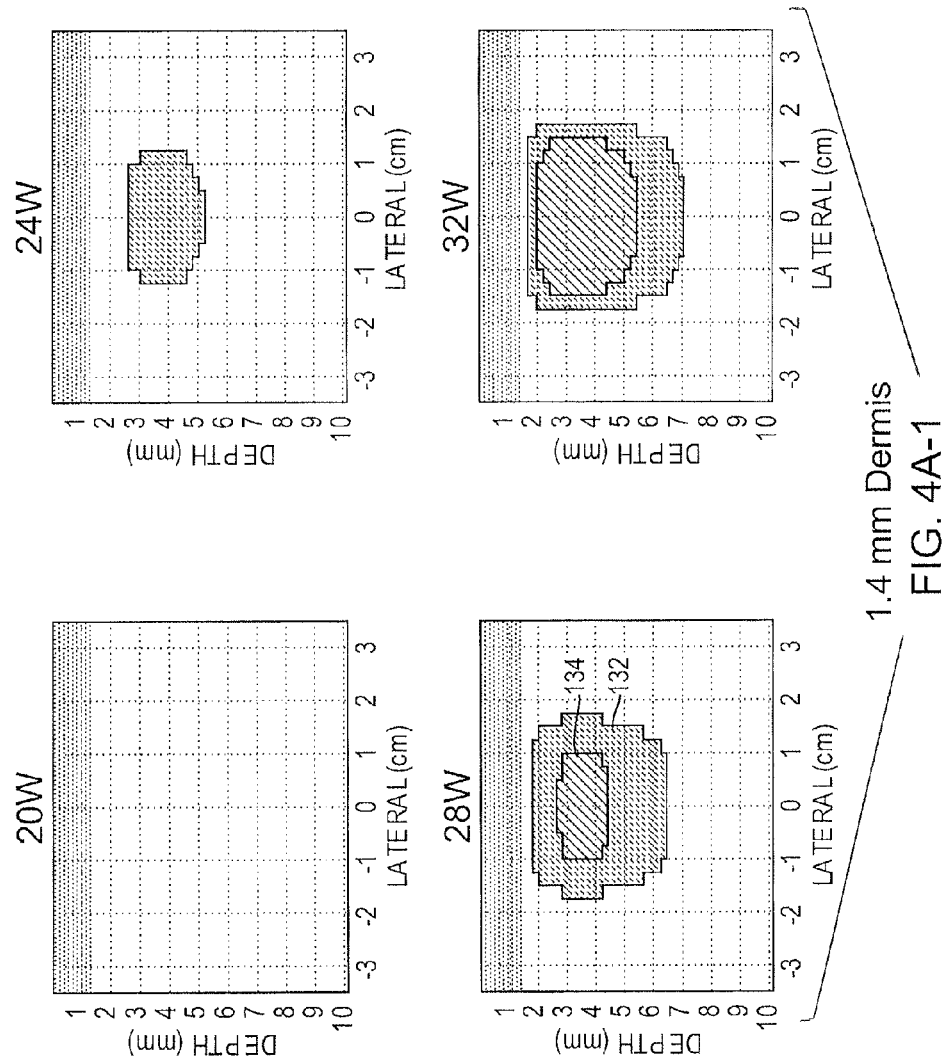
Figures 2, 4A:
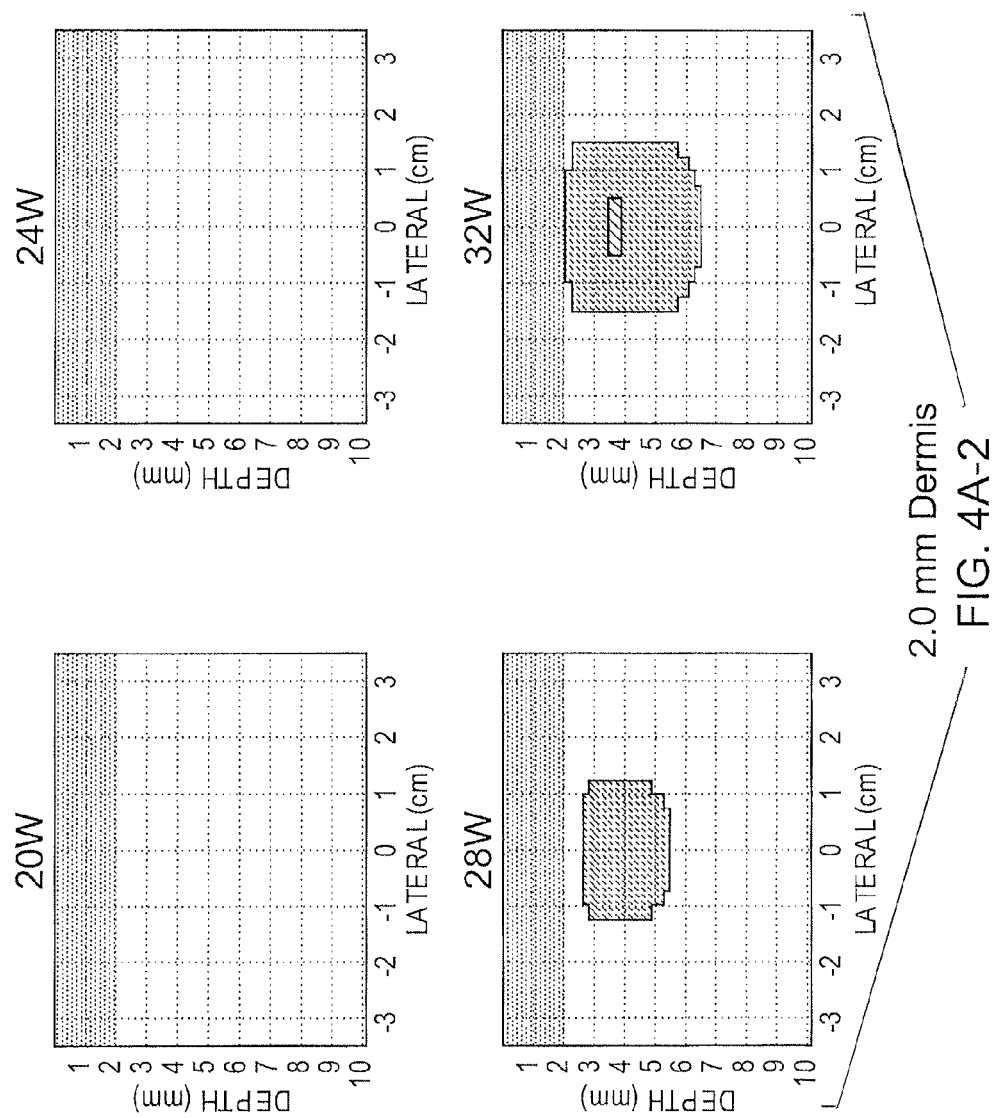
Figures 3, 4A:
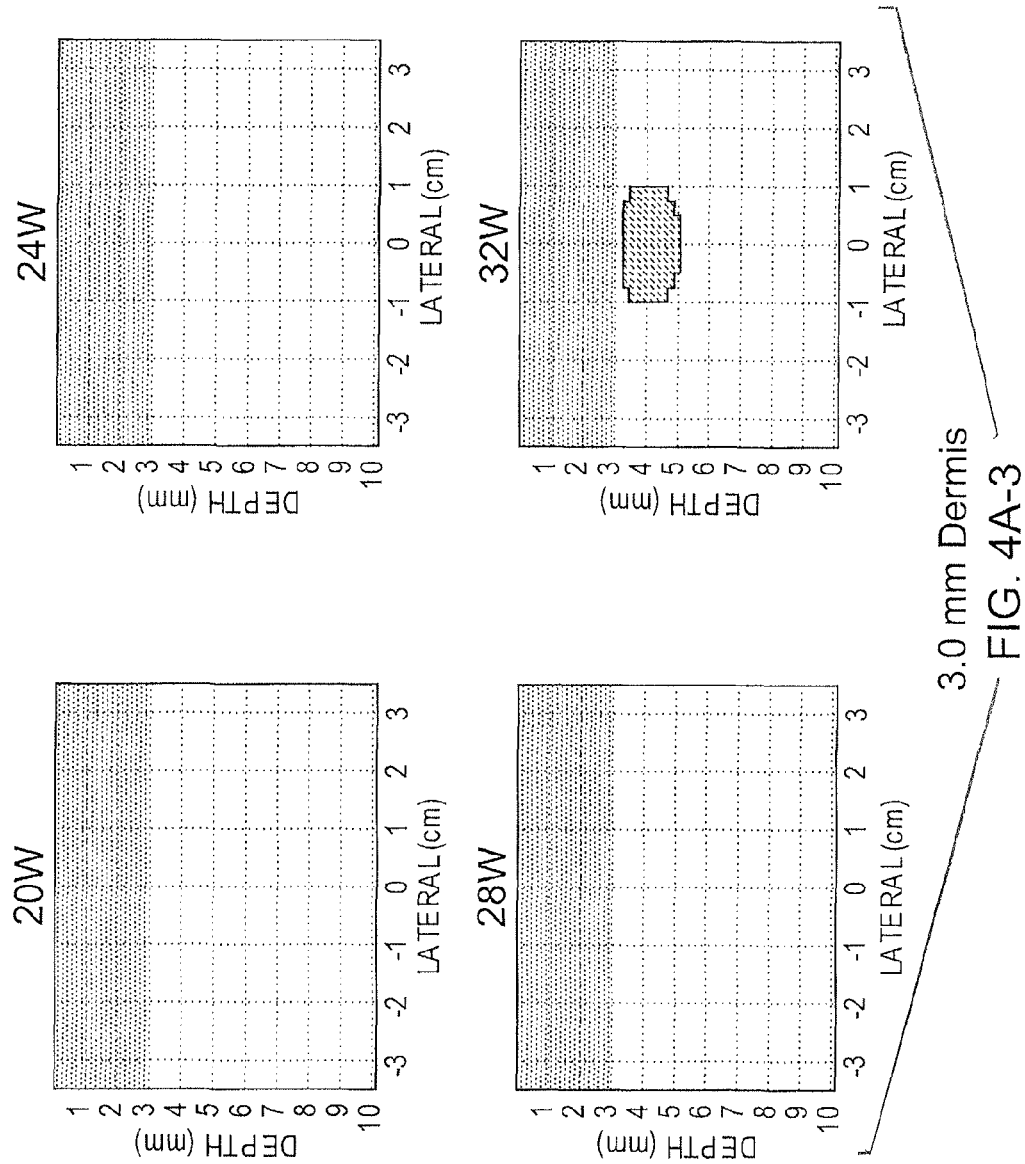

Another example is provided to demonstrate that laser treatment parameters can be customized to subject's skin thickness and tolerance to pain. The dependence of light distribution and resultant temperature rise with dermal thickness. FIGS. 4A-1 to 4A-3 shows changes in zone of thermal damage based on skin thickness when exposed to a 160 s laser pulse at 20 W to 32 W. In FIG. 4A-1, lighter zones 132 denote panniculitis, i.e., inflammation of fatty tissue and most likely apoptosis, while darker zones 136 denote necrosis. As shown, more light reaches the subcutaneous fat layer for thinner dermis. Therefore, when the same laser power density is applied to skin of different dermal thickness, higher temperature and potentially more damage and pain is predicted for thinner dermal thickness. Hence, laser output power and exposure duration can be selected based on a subject's dermal thickness and his/her tolerance to pain. For example, laser power density can be first adjusted to be as high as is tolerated by the subject. Then, the exposure duration can be selected to achieve the desired amount of thermal damage.

Table 2 shows an exemplary calibration chart that provides the power levels and treatment durations for various dermal thickness to achieve the desired threshold for damage. The data in Table 2 is determined based on thermal modeling and measurements on ex-vivo porcine skin and limited human data. As shown, lower power levels are required for thinner-skinned subjects to reach a similar threshold of fat damage as thicker-skinned subjects. However, because more light is capable of reaching the subcutaneous fat region for thinner-skinned subjects, the treatment times are not drastically effected. In some embodiments, if panniculitis, i.e., inflammation of fatty tissue occurs in the subject, increased treatment times in comparison to the times provided in Table 2 are used.

TABLE 2

Relationship between laser power density and treatment time depending on subjects' skin thickness

| Skin Thickness (mm) | Laser Power Density (W/cm$^2$) | Threshold Treatment Time for Damage (s) |
|---|---|---|
| 1.4 | 1.83 | 145 |
|  | 1.91 | 120 |
|  | 1.99 | 105 |
| 2.0 | 1.99 | 185 |
|  | 2.07 | 155 |
|  | 2.15 | 130 |
| 2.4 | 2.15 | 190 |
|  | 2.23 | 155 |
|  | 2.31 | 135 |
| 3.0 | 2.55 | 140 |
|  | 2.63 | 125 |
|  | 2.71 | 110 |

Figure 4B:
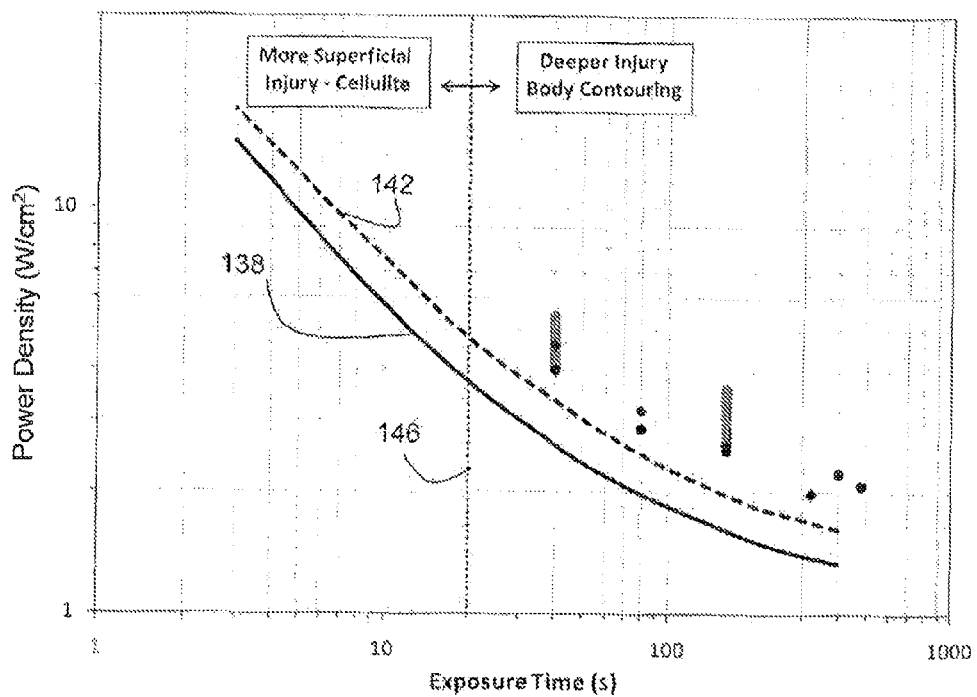

In addition, FIG. 4B illustrates thresholds for necrosis for different skin thickness. Curves 138 and 142 represent the thresholds for necrosis of subcutaneous fatty tissue for 1.5 mm and 2.5 mm thick skin, respectively. The curves are calculated based on finite-element models of 1210 nm radiation applied incidentally on skin surface with concurrent 5° C. surface cooling. For the finite-element calculation, a two-layer model is used with skin as the upper first layer and fatty tissue as the lower second layer. Based on the two-layer model, a standard Monte Carlos simulation is used to determine the fractional percent absorption occurring within each volume element in the model. When combined with the incident fluence, the Monte Carlos simulation can be used to compute the rate of heating in each volume element. In some embodiments, a curve representing an upper bound for necrosis corresponding to each skin thickness can also be determined.

For every skin thickness, higher power densities at shorter exposure durations, which are in the area to the left of the line 146, create more superficial injury. In contrast, longer exposure times at lower power densities, which are in the area to the right of the line 146, create a deeper zone of injury.

In addition, data points represented by the solid circles in FIG. 4B indicate the threshold of necrosis as measured by a lack of nitroblue tetrazolium chloride (NBTC) stains in laser-treated excised pig skin. Each excised skin sample was about 2 cm thick with dermis about 2 mm to about 3 mm thick. Samples were placed on a hot plate heated to 35° C. before exposure to laser treatment. Data points represented by the solid diamonds indicate the threshold of necrosis measured in live pigs. Necrosis in the subcutaneous fatty tissue of the pig tissue were determined based on biopsies taken two days following laser treatment and staining with NBTC. Data points represented by the solid bars indicate the therapeutic range when treating abdominal skin in human volunteers for 40 s and 160 s exposures. The lowest end of each of the bars represents the lowest power density used where fat necrosis was observed. The uppermost end of each bar represents the highest power density used before adverse skin effects are observed.

Yet another example is provided to show that thermal damage is dependent on both the applied laser power and the treatment duration time. In this example, laser damage was measured in freshly excised porcine skin. Skin samples were cut to about 50 mm squares, each about 15 mm thick. Skin thickness was about 2 mm. Samples were warmed to 35° C. The samples are then placed with skin side up on top of an aluminum hot plate and heated to 35° C. The laser sequence was initiated by a foot switch pushed immediately after a laser treatment handpiece was centered on the samples and placed in contact with the skin surface. Samples were treated with laser power densities varying from 1.9 W/cm$^2$ to 2.9 W/cm$^2$ (24 W to 36 W for 40 mm spot size) for 80 s to 200 s. In addition, surface cooling is applied during laser treatment of the samples.

Following the laser treatment, 40 mm by 7 mm slices were cut from the center of the laser treated area of each sample and placed in 4 ml of a stock nitroblue tetrazolium chloride (NBTC) solution that was diluted 1:5. The sample remained in solution for 3 hours at room temperature, after which the sample is removed and placed in 10% neutral buffered formalin.

Figure 5:
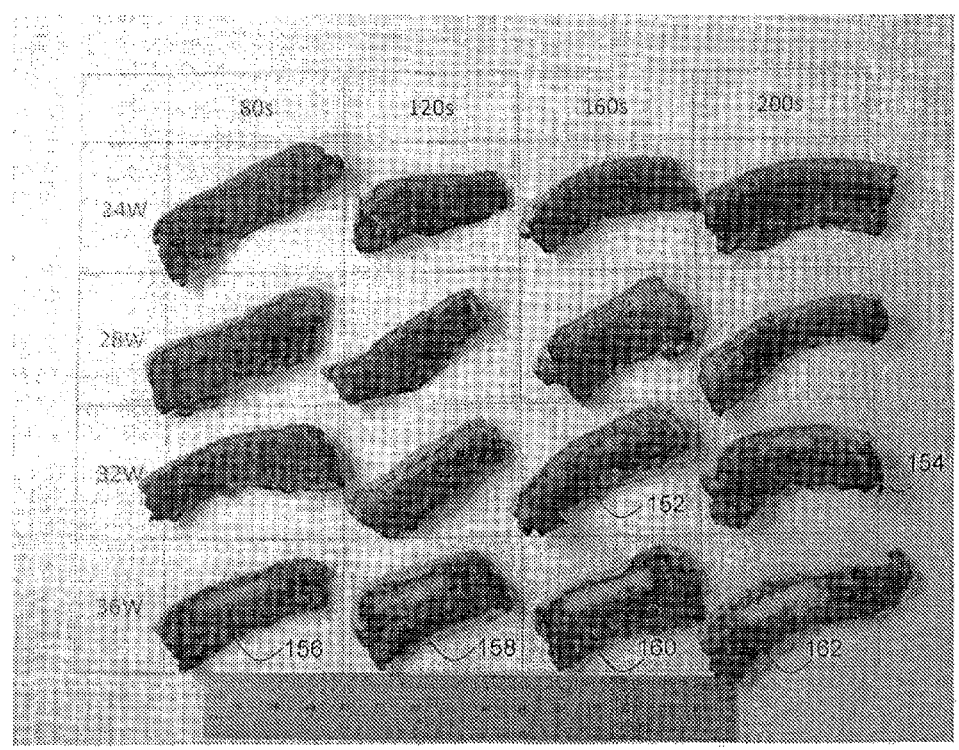
FIG. 5 shows tissue samples treated.

The NBTC-stained samples are shown in FIG. 5. Thermal damage is indicated by loss of staining due to the inability of NADPH-diaphorase (a mitochondrial enzyme) to reduce NBTC to a blue water insoluble pigment, formazan. Hence, decreased staining corresponds to decreased mitochondrial function, which indicates necrosis. As shown, a zone of light NBTC staining can be observed in the samples 152, 154 treated at 32 W (2.5 W/cm$^2$ for 40 mm spot size) for 160 s and 200 s and in the samples 156, 158, 160 and 162 for all time durations when treated at 36 W (2.9 W/cm$^2$ for 40 mm spot size). Therefore, the amount of thermal damage is dependent on both the applied laser power and the treatment duration time. In addition, good staining was observed in the dermis of all the samples, demonstrating that the dermis is spared from damage by surface cooling.

In another example, effective pain-tolerant power densities, peak dermal temperatures, and depths of peak temperatures are provided for various treatment wavelengths and skin thickness. In particular, Table 3 illustrates the effective pain-tolerant power densities, peak dermal temperatures, and depths of peak temperatures for both fat-selective and non fat-selective wavelengths and for skin thickness of 1.5 mm, 2.0 mm, and 2.5 mm. The laser exposure duration is about 280 seconds.

TABLE 3

Treatment parameters for various wavelengths and skin thickness

| | 1.5 mm skin | | | 2.0 mm skin | | | 2.5 mm skin | | |
|---|---|---|---|---|---|---|---|---|---|
| λ (mm) | Power Density (W/cm²) | Peak Dermal Temp (° C.) | Peak Temp Depth (mm) | Power Density (W/cm²) | Peak Dermal Temp (° C.) | Peak Temp Depth (mm) | Power Density (W/cm²) | Peak Dermal Temp (° C.) | Peak Temp Depth (mm) |
| 924* | 3.2 | 38 | 4.9 | 3.4 | 40 | 4.7 | 3.4 | 41 | 4.5 |
| 975 | | | | 3.5 | 42 | 4.7 | | | |
| 1064 | | | | 4.0 | 40 | 4.9 | | | |
| 1140 | | | | 3.0 | 42 | 4.5 | | | |
| 1210* | 2.1 | 43 | 3.7 | 2.2 | 43 | 3.7 | 2.3 | 43 | 3.7 |

In Table 3, the 924 nm and the 1210 nm wavelengths are fat-selective wavelengths, which are preferentially absorbed by lipid cells. The 975 nm, 1064 nm and 1140 nm wavelengths are non fat-selective wavelengths. As shown, the peak dermal temperature is below 44° C. for all treatment wavelengths and skin thickness. In addition, the power density of the applied can be adjusted based on skin thickness.

Figure 6B:
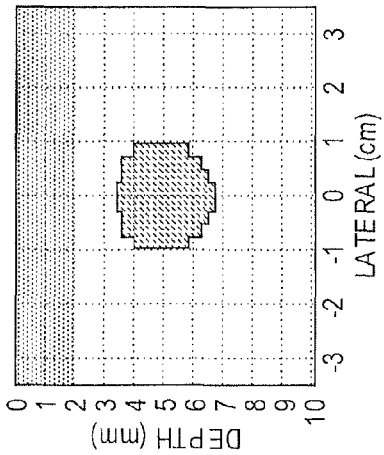
FIG. 6A-F show & experimental and computation results for treating fatty tissue.
Figure 6D:
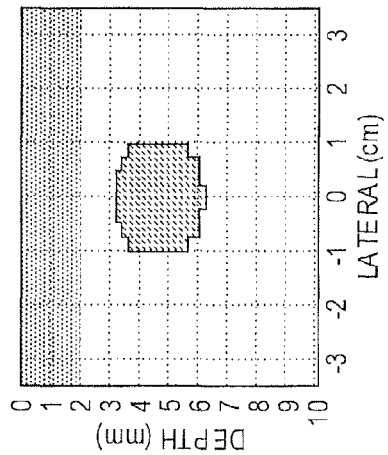
Figure 6A:
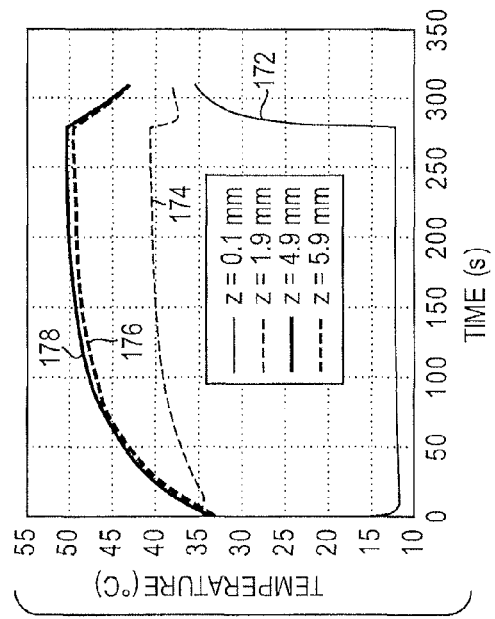
Figure 6C:
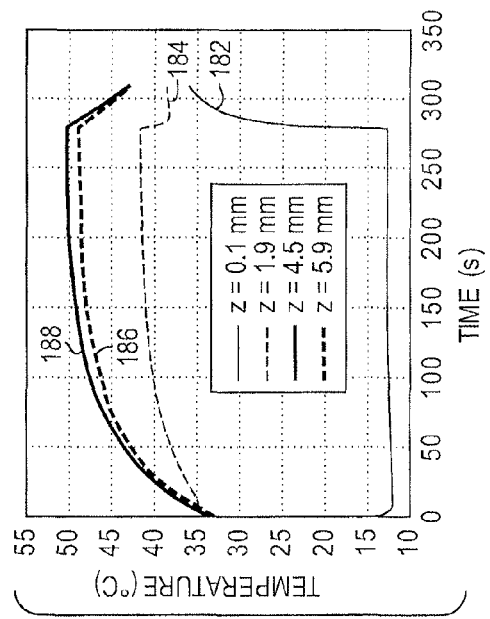
Figure 6F:
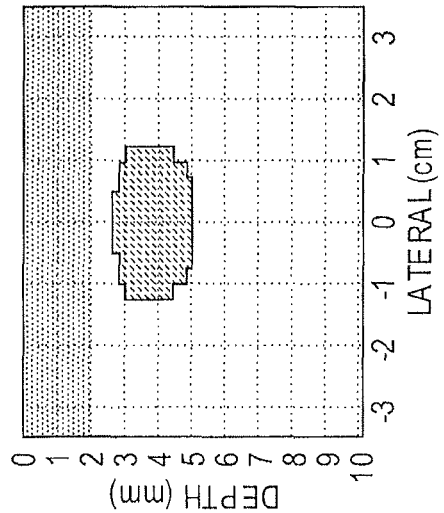
Figure 6E:
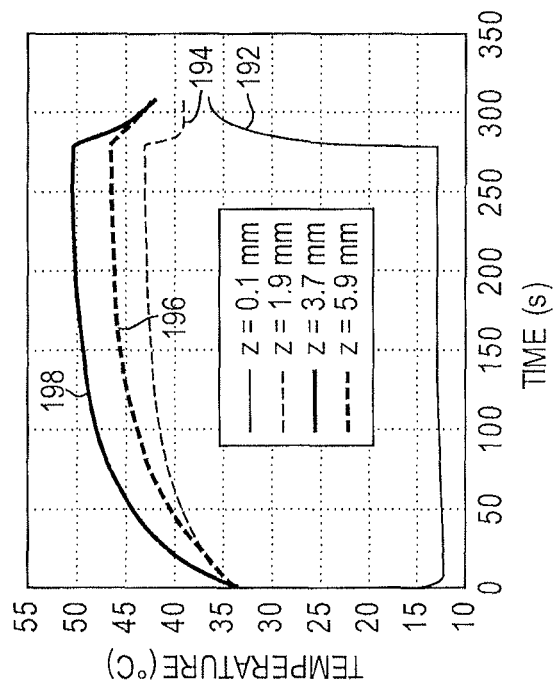

FIGS. 6A-F show temperature profiles and predicted thermal damage for treating 2.0 mm-thick skin at various wavelengths and power densities. In particular, FIGS. 6A-B show the temperature profiles at various skin depths and predicted thermal damage, respectively, when the skin is treated at a power density of 4.0 W/cm² and a wavelength of 1064 nm, which is a non fat-selective wavelength. In FIG. 6A, temperature profiles 172, 174, 176, and 178 correspond to depth of 0.1 mm, 1.9 mm, 4.9 mm, and 5.9 mm, respectively. FIGS. 6C-D show the temperature profiles at various skin depths and predicted thermal damage, respectively, when the skin is treated at a power density of 2.9 W/cm² and a wavelength of 1140 nm, which is also a non fat-selective wavelength. In FIG. 6C, temperature profiles 182, 184, 186, and 188 correspond to depth of 0.1 mm, 1.9 mm, 4.9 mm, and 5.9 mm, respectively. FIGS. 6E-F show the temperature profiles at various skin depths and predicted thermal damage, respectively, when the skin is treated at a power density of 2.0 W/cm² and a wavelength of 1210 nm, which is a fat-selective wavelength. In FIG. 6E, temperature profiles 192, 194, 196, and 198 correspond to depth of 0.1 mm, 1.9 mm, 4.9 mm, and 5.9 mm, respectively. The profiles 178, 188 and 198 of FIGS. 6A, C and E, respective, demonstrate that the peak temperatures in the subcutaneous fat region for all the sample treatment parameters are about 50° C., which is sufficient to cause thermal damage to the subcutaneous fat region.

Figure 7:
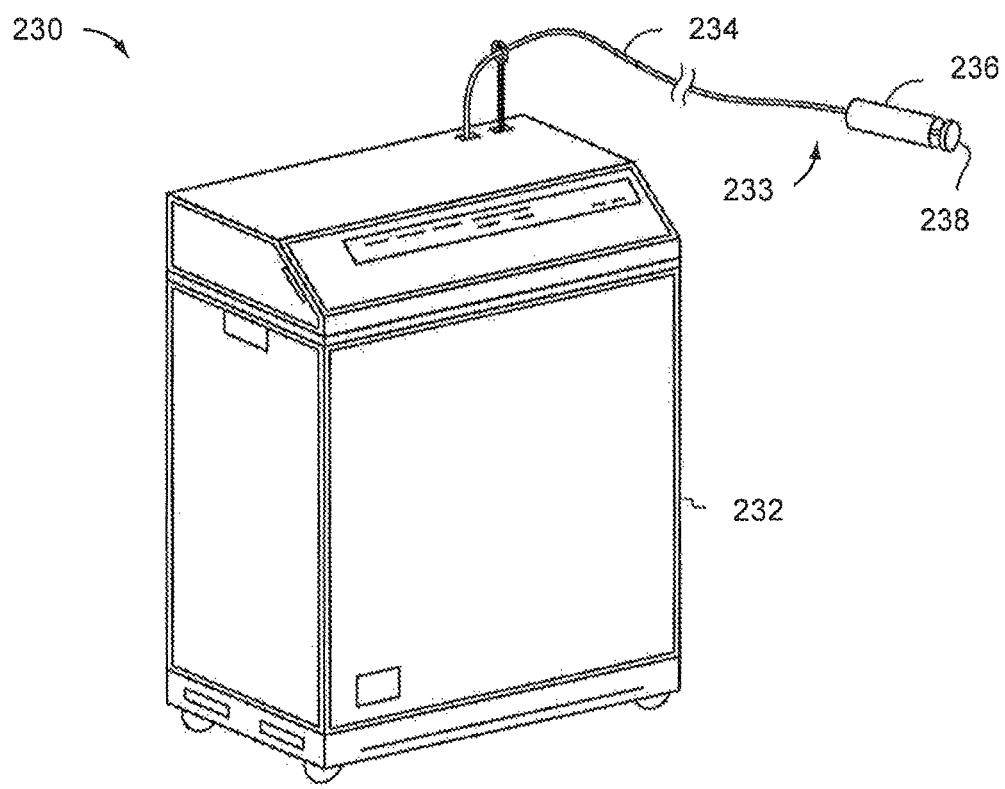
FIG. 7 shows an exemplary embodiment of a system for treating fatty tissue.

FIG. 7 shows an exemplary embodiment of a system 230 for treating tissue. The system 230 can be used to non-invasively deliver a beam of radiation to a target region. For example, the beam of radiation can be delivered through an external surface of skin over the target region. The system 230 includes an energy source 232 and a delivery system 233. In one embodiment, a beam of radiation provided by the energy source 232 is directed via the delivery system 233 to a target region. In the illustrated embodiment, the delivery system 233 includes a fiber 234 having a circular cross-section and a handpiece 236. A beam of radiation can be delivered by the fiber 234 to the handpiece 236, which can include an optical system (e.g., an optic or system of optics) to direct the beam of radiation to the target region. A user can hold or manipulate the handpiece 36 to irradiate the target region. The delivery system 233 can be positioned in contact with a skin surface, can be positioned adjacent a skin surface, can be positioned proximate a skin surface, can be positioned spaced from a skin surface, or a combination of the aforementioned. In the embodiment shown, the delivery system 233 includes a spacer 238 to space the delivery system 233 from the skin surface. A spacer 238 is not required however. In one embodiment, the spacer 238 can be a distance gauge, which can aid a practitioner with placement of the delivery system 233.

Referring to FIG. 7, to minimize unwanted thermal injury to tissue not targeted (e.g., an exposed surface of the target region and/or the epidermal layer), the delivery system 233 shown in FIG. 7 includes a cooling system for cooling before, during or after delivery of radiation, or a combination of the aforementioned. Cooling can include contact conduction cooling, evaporative spray cooling (using a solid, liquid, or gas), convective air flow cooling, or a combination of the aforementioned. If cooling is used, it can cool the most superficial layers of epidermal tissue. Cooling can facilitate leaving the epidermis intact.

Figure 8:
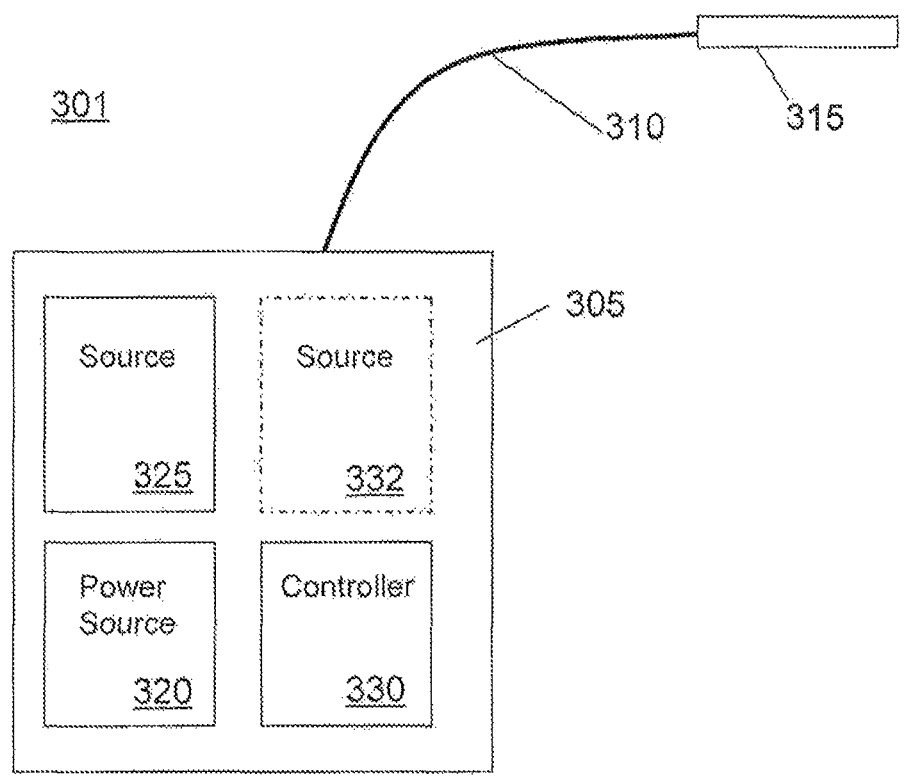
FIG. 8 shows another exemplary embodiment of a system that can be used for treating fatty tissue.

FIG. 8 shows an exemplary embodiment of a system 301 that can be used to form a pattern of treatment zones in skin. System 301 can include a base unit 305 coupled to an umbilicus 310, which is connected to a delivery module 315. The base unit 305 includes a power source 320 that supplies power to an energy source 325. The base unit 305 also includes a controller 330, which can be coupled to a user interface and can include a processing unit.

The system 301 can be used to non-invasively deliver an array of radiation beams to a target region of the skin. For example, the array of radiation beams can be delivered through an external surface of skin over the target region. In one embodiment, a beam of radiation provided by the energy source 325 is directed via the delivery module 315 to a target region. The umbilicus 310 can act as a conduit for communicating power, signal, fluid and/or gas between the base unit 305 and the delivery module 315. The umbilicus 310 can include a fiber to deliver radiation from the base unit 305 to the delivery module 315. The delivery module 315 can include an optical system (e.g., an optic or a system of optics) to convert the beam into an array of radiation beams and direct the array to the target region. The delivery module 315 can include one or more laser diodes or light emitting diodes, or include one or more optical fibers delivering light from a source such as laser diodes. The optical system can include a mask or focusing system to provide a beam of radiation having regions where no treatment radiation is delivered (e.g., to create a pattern of undamaged tissue or skin surrounded by damaged tissue or skin). A user can hold or manipulate the delivery module 315 to irradiate the target region. The delivery module 315 can be positioned in contact with a skin surface, can be positioned adjacent a skin surface, can be positioned proximate a skin surface, can be positioned spaced from a skin surface, or a combination of the aforementioned. In some embodiments, an array of radiation beams can be formed from a single beam of radiation by a system of optics.

In some embodiments, the base unit 305 can have a second source 332 of radiation. For example, the source 325 can provide radiation that is absorbed preferentially in the dermal skin region, and the second source 332 can provide radiation that is absorbed preferentially in the subcutaneous fat region.

To minimize unwanted thermal injury to tissue not targeted (e.g., an exposed surface of the target region and/or the epidermal layer), the delivery module 315 can include a cooling module for cooling before, during or after delivery of radiation, or a combination of the aforementioned. Cooling can include contact conduction cooling, evaporative spray cooling, convective air flow cooling, or a combination of the aforementioned.

Figure 9:
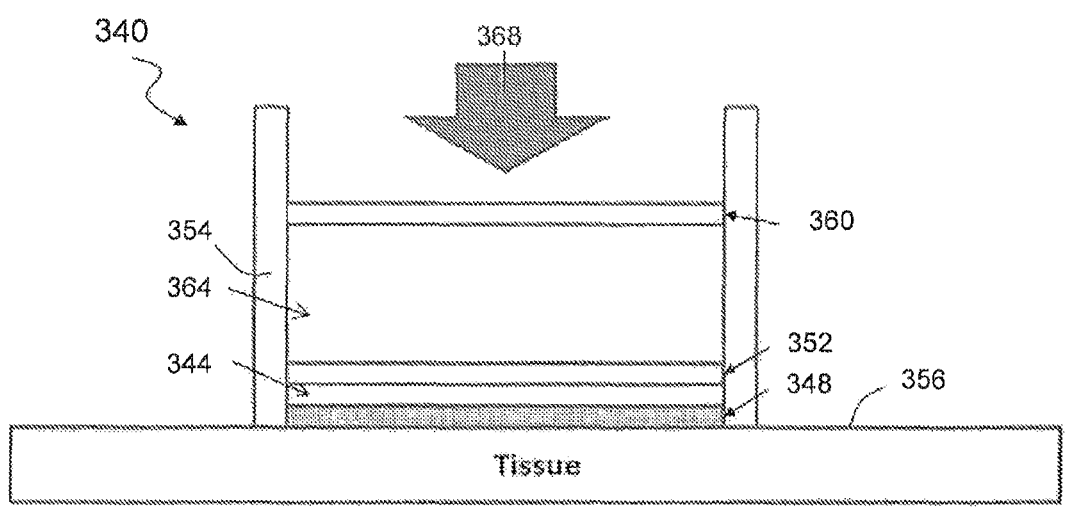
FIG. 9 shows an exemplary skin contacting portion of a delivery module.

FIG. 9 shows an exemplary skin contacting portion 340, which can be a portion of the system 230 attached to the handpiece 236 or the delivery module 315. The skin contacting portion 340 can include a coolant chamber 344 formed by two optical windows 348, 352 and sidewalls 354. Cooled refrigerant is passed through the flow chamber 344, cooling the window 348 that is in contact with a surface of skin 356, thereby cooling the skin surface 356. One disadvantage of a one-chamber design is that it also cools the exterior of the windows 348, 352, which can lead to water droplets or frost forming on the exterior of the windows 348, 352 due to condensation of atmospheric water vapor. Condensation is generated depending on the temperature of the refrigerant and relative humidity. To avoid condensation, the skin contacting portion 340 includes a third window 360 to form a second chamber 364 defined by the windows 352, 360 and the sidewalls 354. The second chamber 364 can be filled with either a thermally insulating gas, such as argon, krypton, or dry nitrogen. In some embodiments, the second chamber 364 is fully or partially evacuated.

The first optical window 348 can be made from a substance that has good thermal conductivity such as crystalline sapphire. Each of the windows 348, 352 and 360 can be a sapphire or glass window. All of the windows 348, 352 and 360 as well as the chilled coolant fluid in the coolant chamber 344 can be transparent to the intended wavelength(s) of the applied laser 368.

In some embodiments, the coolant chamber 344 can allow flow of chilled coolant. The coolant can be chilled water, a fluorocarbon type cooling fluid such as chilled Fluorinert, a cryogenic fluid, or the like. The coolant can be transparent to the radiation used during treatment. The coolant chamber 344 can have sufficient flow to avoid a significant increase in the water temperature in the chamber. The coolant chamber 344 can be a thin chamber, which increases flow velocity. The coolant chamber 344 can include plenums and ports to avoid eddies within the chamber 344. For some laser wavelengths where the coolant can absorb the laser radiation, the coolant chamber 344 can be made sufficiently thin to avoid excessive absorption of the laser energy by water in the chamber.

The second chamber 364 can be purged, filled with argon, and sealed. Alternatively, the second chamber 364 can be evacuated and filled with krypton or some other thermally insulating gas.

The upper and lower surfaces of the window 360 can be coated with an antireflective film chosen to minimize reflection at the laser wavelength(s). The upper surface of the window 352, which is the surface facing the second chamber 364, can be coated with an antireflective film chosen to minimize reflection at the laser wavelength(s).

In various embodiments, the energy source 332 can be an incoherent light source or a coherent light source (e.g., a laser). The energy source 332 can be broadband or monochromatic. The beam of radiation can be a pulsed beam, a scanned beam, or a gated continuous wave (CW) beam. The laser can be a diode laser, a solid state laser, a fiber laser, or the like. An incoherent source can be a light emitting diode (LED), a flashlamp (e.g., an argon or xenon lamp), an incandescent lamp (e.g., a halogen lamp), a fluorescent light source, or an intense pulsed light system. The incoherent source can include appropriate filters to block unwanted electromagnetic radiation.

In various embodiments, the wavelength of the electromagnetic radiation can be about 400 nm to about 4000 nm, although longer and shorter wavelengths can be used depending on the application. In certain embodiments, the wavelength of the electromagnetic radiation is fat selective. For example, the ratio of coefficients of absorption of fat to water is about 0.5 or greater. The wavelength can be about 875 nm to about 950 nm or about 1175 nm to about 1250 nm. For example, the wavelength can be about 900 nm to about 940 nm or about 1200 nm to about 1240 nm. The wavelength can be about 1200 nm to about 1230 nm. In some embodiments, the wavelength is about 1210 nm. A first source operating at about 1210 nm can be combined with a second source operating from about 400 nm to about 10.6 microns, with an RF source, or with an ultrasonic source.

In some embodiments, the wavelength is non-fat selective, e.g., about 950 nm to about 1090 nm, about 1100 nm to about 1160 nm, about 1,300 nm to about 1625 nm or about 1,800 nm to about 2,200 nm.

In some embodiments, the wavelength is selected to penetrate a surface of skin and reach the underlying subcutaneous fat region without being absorbed along the way so as to cause damage to the fat cells in the subcutaneous fat region.

In various embodiments, an average power density of between about 0.5 W/cm$^2$ to about 5 W/cm$^2$ of the electromagnetic radiation can be delivered to the skin surface to treat the subcutaneous fat region for about 40 seconds or longer, such as about 40 seconds to about 600 seconds. In some embodiments, the average power density is less than or equal to about 2 W/cm$^2$, such as about 0.5 W/cm$^2$ to about 2 W/cm$^2$. In some embodiments, the radiation is delivered to the subcutaneous fat region for at least about 300 seconds, such as about 300 seconds to about 400 seconds. The peak power density of the applied radiation can exceed 2 W/cm$^2$, as long as the average power density over a treatment period is less than or equal to about 2 W/cm$^2$. In some embodiments, multiple pulses of radiation can be delivered to the subcutaneous fat region and the sum of the pulse durations reaches the desired treatment duration.

In various embodiments, the beam of radiation can have a fluence of about 50 J/cm$^2$ to about 1500 J/cm$^2$, although larger or smaller fluence can be used depending on the application. The laser power can be about 5 W to about 100 W, although higher or lower power can be used depending on the application. In some examples, the laser power can be about 20 W to about 50 W depending on the size of the treatment zone, thus allowing between about 0.5 W/cm$^2$ to about 2 W/cm$^2$ to be delivered to the skin surface.

In various embodiments, the beam of radiation can have a spot size between about 10 mm and about 60 mm, although larger and smaller spot sizes can be used depending on the application. In some examples, the spot size is rectangular and about 50 mm by 100 mm in dimension. In certain embodiments, the radiation is delivered simultaneously to a surface of skin overlying the subcutaneous fat region. The surface of skin can have an area of at least 10 cm².

Radiation can be applied to the skin in a stamping mode or by scanning a light source along a surface of the skin. A computerized pattern generator can be used or a handpiece can be manually manipulated to scan the light source.

In various embodiments, the parameters of the radiation can be selected to deliver the beam of radiation to a predetermined depth. In some embodiments, the beam of radiation can be delivered to the target region about 0.005 mm to about 10 mm below an exposed surface of the skin, although shallower or deeper depths can be selected depending on the application. In some embodiments, the depth is about 1 mm to about 3.5 mm. In some embodiments, the depth is greater than or equal to 3 mm below the surface of skin, where the subcutaneous fat region resides.

In various embodiments, the subcutaneous fat region can be heated to a temperature of between about 47° C. and about 80° C., although higher and lower temperatures can be used depending on the application. In one embodiment, the temperature is between about 50° C. and about 55° C. In one embodiment, the temperature is about 50° C.

In various embodiments, the beam of radiation can have exposure duration between about 3 s and about 1800 s, although longer and shorter exposure durations can be used depending on the application. In some embodiments, the beam of radiation can have exposure duration of at least 300 seconds, such as about 300 seconds to about 400 seconds. In some embodiments, a longer exposure time permits a beam of radiation to treat at a greater depth into the subcutaneous fat region in comparison to a beam of radiation having a shorter exposure time, providing that all other parameters are the same. In certain examples, if the power intensity is sharply increased and then lowered during several time intervals, the treatment duration is less than 300 seconds, such as about 140 seconds to about 300 seconds. The treatment time can be even shorter if the power intensity is increased slightly after the lowering period.

An optical system can be used to deliver radiation to a large area beam or as a pattern of beamlets (e.g., a plurality of microbeams having a spotsize of about 0.1-2 mm) to form a pattern of thermal injury within the biological tissue.

One or more sensors can be positioned relative to a target region of skin. For example, a sensor can be positioned in contact with, spaced from, proximate to, or adjacent to the skin target. A sensor can determine a temperature on a surface of the target region, in the target region, or remote from the target region. The sensor can be a thermistor, an array of thermistors, a thermopile, a thermocouple, a thermometer, a resistance thermometer, and a thermal-imaging based sensor, a thermographic camera, an infrared camera or any combination of the aforementioned.

Processors suitable for the execution of computer programs include, by way of example, both general and special purpose microprocessors, and any one or more processors of any kind of digital computer. A processor can receive instructions and data from a read-only memory or a random access memory or both. A processor also includes, or be operatively coupled to receive data from or transfer data to, or both, one or more mass storage devices for storing data, e.g., magnetic, magneto-optical disks, or optical disks. Data transmission and instructions can also occur over a communications network.

Information carriers suitable for embodying computer program instructions and data include all forms of non-volatile memory, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in special purpose logic circuitry.

The treatment radiation can damage one or more fat cells so that at least a portion of lipid contained within can escape or be drained from the treated region. At least a portion of the lipid can be carried away from the tissue through biological processes. In one embodiment, the body's lymphatic system can drain the treated fatty tissue from the treated region. In an embodiment where a fat cell is damaged, the fat cell can be viable after treatment. In one embodiment, the treatment radiation can destroy one or more fat cells. In one embodiment, a first portion of the fat cells is damaged and a second portion is destroyed. In one embodiment, a portion of the fat cells can be removed to selectively change the shape of the body region.

In some embodiments, the beam of radiation can be delivered to the target region to thermally injure, damage, and/or destroy one or more fat cells. For example, the beam of radiation can be delivered to a target chromophore in the target region. Suitable target chromophores include, but are not limited to, a fat cell, lipid contained within a fat cell, fatty tissue, a wall of a fat cell, water in a fat cell, and water in tissue surrounding a fat cell. The energy absorbed by the chromophore can be transferred to the fat cell to damage or destroy the fat cell. For example, thermal energy absorbed by dermal tissue can be transferred to the fatty tissue. In one embodiment, the beam of radiation is delivered to water within or in the vicinity of a fat cell in the target region to thermally injure the fat cell.

In various embodiments, treatment radiation can affect one or more fat cells and can cause sufficient thermal injury in the dermal region of the skin to elicit a healing response to cause the skin to remodel itself. This can result in more youthful looking skin and an improvement in the appearance of cellulite. In one embodiment, sufficient thermal injury induces fibrosis of the dermal layer, fibrosis on a subcutaneous fat region, or fibrosis in or proximate to the dermal interface. In one embodiment, the treatment radiation can partially denature collagen fibers in the target region. Partially denaturing collagen in the dermis can induce and/or accelerate collagen synthesis by fibroblasts. For example, causing selective thermal injury to the dermis can activate fibroblasts, which can deposit increased amounts of extracellular matrix constituents (e.g., collagen and glycosaminoglycans) that can, at least partially, rejuvenate the skin. The thermal injury caused by the radiation can be mild and only sufficient to elicit a healing response and cause the fibroblasts to produce new collagen. Excessive denaturation of collagen in the dermis causes prolonged edema, erythema, and potentially scarring. Inducing collagen formation in the target region can change and/or improve the appearance of the skin of the target region, as well as thicken the skin, tighten the skin, improve skin laxity, and/or reduce discoloration of the skin.

In various embodiments, a zone of thermal injury can be formed at or proximate to the dermal interface. Fatty tissue has a specific heat that is lower than that of surrounding tissue (fatty tissue, so as the target region of skin is irradiated, the temperature of the fatty tissue exceeds the temperature of overlying and/or surrounding dermal or epidermal tissue. For example, the fatty tissue has a volumetric specific heat of about 1.8 J/cm$^3$ K, whereas skin has a volumetric specific heat of about 4.3 J/cm$^3$ K. In one embodiment, the peak temperature of the tissue can be caused to form at or proximate to the dermal subcutaneous fat interface. For example, a predetermined wavelength, fluence, pulse duration, and cooling parameters can be selected to position the peak of the zone of thermal injury at or proximate to the dermal subcutaneous fat interface. This can result in collagen being formed at the bottom of the dermis and/or fibrosis at or proximate to the dermal interface. As a result, the dermal interface can be strengthened against fat herniation. For example, strengthening the dermis can result in long-term improvement of the appearance of the skin since new fat being formed or untreated fat proximate the dermal interface can be prevented and/or precluded from crossing the dermal interface into the dermis. Targeted heating at the dermal subcutaneous fat interface can also affect the base of eccrine and/or apocrine glands to reduce sweating, thus helpful to subjects with hyperhidrosis.

In one embodiment, fatty tissue is heated by absorption of radiation, and heat can be conducted into dermal tissue proximate the fatty tissue. The fatty tissue can be disposed in the dermal tissue and/or can be disposed proximate to the dermal interface. A portion of the dermal tissue (e.g., collagen) can be partially denatured or can suffer another form of thermal injury, and the dermal tissue can be thickened and/or be strengthened as a result of the resulting healing process. In such an embodiment, a fat-selective wavelength of radiation can be used.

In one embodiment, water in the dermal tissue is heated by absorption of radiation. The dermal tissue can have disposed therein fatty tissue and/or can be overlying fatty tissue. A portion of the dermal tissue (e.g., collagen) can be partially denatured or can suffer another form of thermal injury, and the dermal tissue can be thickened and/or be strengthened as a result of the resulting healing process. A portion of the heat can be transferred to the fatty tissue, which can be affected. In one embodiment, water in the fatty tissue absorbs radiation directly and the tissue is affected by heat. In such embodiments, a water selective wavelength of radiation can be used.

In various embodiments, a treatment can cause minimal cosmetic disturbance so that a subject can return to normal activity following a treatment. For example, a treatment can be performed without causing discernible side effects such as bruising, open wounds, burning, scarring, or swelling. Furthermore, because side effects are minimal, a subject can return to normal activity immediately after a treatment or within a matter of hours, if so desired.

In various embodiments, an ultrasound device can be used to measure the depth or position of the fatty tissue. For example, a high frequency ultrasound device operating at 10 MHz to 20 MHz can be used. A handpiece of an ultrasound device can be placed proximate to the skin to make a measurement. In one embodiment, the ultrasound device can be placed in contact with the skin surface. The ultrasound device can deliver ultrasonic energy to measure position of the dermal interface, so that radiation can be directed to the interface.

The time duration of the cooling and of the radiation application can be adjusted so as to maximize the thermal injury to the vicinity of the dermal interface or overlying epidermal and dermal tissue. For example, if the position of the fatty tissue is known, then parameters of the optical radiation, such as pulse duration and/or fluence, can be optimized for a particular treatment. Cooling parameters, such as cooling time and/or delay between a cooling and irradiation, can also be optimized for a particular treatment. Accordingly, a zone of thermal treatment can be predetermined and/or controlled based on parameters selected. For example, the zone of thermal injury can be positioned in or proximate to the dermal interface.

In various embodiments, the skin in the target region or adjacent to the target region can be massaged and/or vibrated before, during, and/or after irradiation of the target region of skin. The massage can be a mechanical massage or can be manual massage. A handpiece can include rollers to massage the skin. Radiation can be delivered through a central portion of the handpiece. The massage handpiece can be adapted to fit over the delivery system shown in FIG. 6. In one embodiment, a delivery system can be formed with a mechanical massage device affixed. In one embodiment, vacuum can be used to pull the tissue into the device, which can provide an additional massage effect. In one embodiment, a person massages the target region of skin after irradiation of the tissue. Massaging the target region of skin can facilitate removal of the treated fatty tissue from the target region. For example, massaging can facilitate draining of the treated fatty tissue from the treated region. Vibrating and/or massaging the skin in the target region or adjacent to the target region during irradiation can reduce or alleviate treatment pain and allow treatment using higher power densities.

In various embodiments, vacuum can be used to ensure that the skin surface through which the treatment beam passes is in good contact with the sapphire cooling window during surface cooling. This ensures safer treatment. In addition, vacuum can be used to hold the treatment applicator in place, thereby providing hand-free treatment. This is particularly useful when treatment times are long.

While the invention has been particularly shown and described with reference to specific illustrative embodiments, it should be understood that various changes in form and detail may be made without departing from the spirit and scope of the invention.

The invention claimed is:

1. A method of treating a subcutaneous fat region, comprising:
generating electromagnetic radiation having a wavelength of 1,200 nm to 1,230 nm;
delivering an average power density of less than or equal to 2.3 W/cm$^2$ of the electromagnetic radiation to the subcutaneous fat region for at least 300 seconds,
causing a peak temperature within the subcutaneous fat region, and
treating at least one fat cell in the subcutaneous fat region at the peak temperature resulting in necrosis of the at least one fat cell,
wherein, to prevent exceeding a predetermined temperature, the electromagnetic radiation is delivered to the subcutaneous fat region in at least two consecutive first and second time intervals, and during the first time interval, the subcutaneous fat region is exposed to the electromagnetic radiation at a first power density, and during the second time interval, the subcutaneous fat region is exposed to the electromagnetic radiation at a second power density continuously reduced from the first power density, wherein the first time interval is shorter than the second time interval; and
exposing the subcutaneous fat region at the second power density for a third time interval, wherein the first time interval is shorter than the sum of the second and third time intervals.

2. The method of claim 1 further comprising delivering the electromagnetic radiation to the subcutaneous fat region for 300 seconds to 400 seconds.

3. The method of claim 1 wherein the electromagnetic radiation comprises a plurality of pulses of electromagnetic radiation.

4. The method of claim 1 wherein the average power density is 0.5 W/cm² to 2.5 W/cm².

5. The method of claim 1 wherein the peak power density exceeds 2.5 W/cm².

6. The method of claim 1 further comprising delivering the electromagnetic radiation simultaneously to a surface of skin overlying the subcutaneous fat region, the surface of skin having an area of at least 10 cm².

7. The method of claim 1 further comprising delivering the electromagnetic radiation in the absence of precooling of the epidermal region and the portion of the dermal region overlying the subcutaneous fat region.

8. The method of claim 1 further comprising delivering the electromagnetic radiation in the absence of an anesthetic.

9. The method of claim 1 further comprising damaging the at least one fat cell so that lipid contained within can escape and at least a portion of the lipid can be carried away from the subcutaneous fat region.

10. The method of claim 1 further comprising delivering the electromagnetic radiation to the subcutaneous fat region greater than or equal to 3 mm below a surface of skin.

11. The method of claim 1 further comprising massaging a skin region overlying the subcutaneous fat region prior to, during or after delivery of the electromagnetic radiation.

12. The method of claim 1 further comprising adjusting the average power density based on a thickness of skin overlying the subcutaneous fat region.

13. The method according to claim 1 wherein the power density averaged over the first time interval is higher than the power density averaged over the second time interval.

14. The method according to claim 1 wherein a temperature of a dermal region is maintained below 44° C. the while the peak temperature within the subcutaneous fat region is maintained at at least 50° C.

15. The method according to claim 1 wherein during the first time interval the subcutaneous fat region is exposed to the electromagnetic radiation at a first power density.

16. The method according to claim 1 wherein during a second time interval the subcutaneous fat region is exposed to the electromagnetic radiation at the second power density, and wherein a first time interval is shorter than the second time interval.

* * * * *